(12) United States Patent
Shen et al.

(10) Patent No.: US 12,337,077 B2
(45) Date of Patent: Jun. 24, 2025

(54) METHOD FOR CONSTRUCTING BONE MORPHOGENETIC PROTEIN SLOW-RELEASE SYSTEM

(71) Applicant: THE 2ND AFFILIATED HOSPITAL AND YUYING CHILDREN'S HOSPITAL OF WENZHOU MEDICAL UNIVERSITY, Zhejiang (CN)

(72) Inventors: Liyan Shen, Zhejiang (CN); Wenfei Ni, Zhejiang (CN); Yanlin Chen, Zhejiang (CN); Chenqiang Jin, Zhejiang (CN)

(73) Assignee: THE 2ND AFFILIATED HOSPITAL AND YUYING CHILDREN'S HOSPITAL OF WENZHOU MEDICAL UNIVERSITY, Zhejiang (CN)

( * ) Notice: Subject to any disclaimer, the term of this patent is extended or adjusted under 35 U.S.C. 154(b) by 655 days.

(21) Appl. No.: 17/637,804

(22) PCT Filed: Jul. 1, 2021

(86) PCT No.: PCT/CN2021/103960
§ 371 (c)(1),
(2) Date: Feb. 24, 2022

(87) PCT Pub. No.: WO2022/012339
PCT Pub. Date: Jan. 20, 2022

(65) Prior Publication Data
US 2022/0280687 A1 Sep. 8, 2022

(30) Foreign Application Priority Data
Jul. 14, 2020 (CN) .......................... 202010676616.6

(51) Int. Cl.
*A61L 27/06* (2006.01)
*A61L 27/10* (2006.01)
(Continued)

(52) U.S. Cl.
CPC ............... *A61L 27/06* (2013.01); *A61L 27/10* (2013.01); *A61L 27/227* (2013.01); *A61L 27/34* (2013.01);
(Continued)

(58) Field of Classification Search
CPC ...................................... A61L 27/06
See application file for complete search history.

(56) References Cited

U.S. PATENT DOCUMENTS

| 2006/0216494 | A1  | 9/2006  | Furedi-Milhofer et al. |
| 2011/0274744 | A1* | 11/2011 | Picart .............. A61L 29/16 435/402 |

FOREIGN PATENT DOCUMENTS

| CN | 102950102 | 3/2013 |
| CN | 103893826 | 7/2014 |

(Continued)

OTHER PUBLICATIONS

"International Search Report (Form PCT/ISA/210) of PCT/CN2021/103960," mailed on Sep. 13, 2021, with English translation thereof, pp. 1-6.

*Primary Examiner* — Dah-Wei D. Yuan
*Assistant Examiner* — Andrew J Bowman
(74) *Attorney, Agent, or Firm* — JCIPRNET

(57) ABSTRACT

To solve the problem that an excellent carrier material is absent in a storage and use process of the bone morphogenetic protein, based on self-polymerization universality of dopamine, the positively-charged polyelectrolyte, the negatively-charged polyelectrolyte and the ceramic powder with biological activity are integrated onto the titanium base material in a layer-by-layer assembly mode to construct a bone morphogenetic protein slow-release system, so that long-acting slow release, on a lesion part, of the bone morphogenetic protein is achieved. The slow-release system has the advantages of being high in surface modulus, stable, (Continued)

3 day 7 day 14 day resistant to radiation, good in biocompatibility, and the like, can effectively promote osteogenic differentiation of the mesenchymal stem cells, and can be expected to effectively promote bone repair.

7 Claims, 11 Drawing Sheets

(51) Int. Cl.
*A61L 27/22* (2006.01)
*A61L 27/34* (2006.01)
*A61L 27/54* (2006.01)

(52) U.S. Cl.
CPC ......... *A61L 27/54* (2013.01); *A61L 2300/252* (2013.01); *A61L 2300/412* (2013.01); *A61L 2300/602* (2013.01); *A61L 2420/02* (2013.01); *A61L 2420/08* (2013.01); *A61L 2430/02* (2013.01)

(56) References Cited

FOREIGN PATENT DOCUMENTS

| | | |
|---|---|---|
| CN | 104013997 | 9/2014 |
| CN | 107890585 | 4/2018 |
| CN | 111939317 | 11/2020 |

* cited by examiner

METHOD FOR CONSTRUCTING BONE MORPHOGENETIC PROTEIN SLOW-RELEASE SYSTEM

CROSS-REFERENCE TO RELATED APPLICATION

This application is a 371 of international application of PCT application serial no. PCT/CN2021/103960, filed on Jul. 1, 2021, which claims the priority benefit of China application no. 202010676616.6, filed on Jul. 14, 2020. The entirety of each of the above-mentioned patent applications is hereby incorporated by reference herein and made a part of this specification.

1. TECHNICAL FIELD

The present invention relates to preparation of a protein slow-release system, in particular to a method for constructing a bone morphogenetic protein slow-release system.

2. DESCRIPTION OF RELATED ART

The bone morphogenetic protein (BMP), as an important factor for promoting in-vivo osteogenesis, can induce undifferentiated mesenchymal stem cells across species to proliferate and differentiate to osteoblast, so that osteogenesis is promoted to be widely applied to the fields of maxillofacial bone defect repair, oral implantology, plastic surgery, and the like. However, at present, the application process has the following problems:
  1) The BMP is easy to diffuse quickly in a body fluid, and is also easily decomposed by protease, so that a therapeutic concentration is difficult to maintain, and the BMP cannot act on more target cells within effective time. As a result, the activity of inducing is difficult to bring into full play.
  2) An invasive process is generally required for periodically giving the BMP, for example injection or transfusion which may be painful and troublesome methods. In addition, it is impractical and expensive to constantly give the BMP on a large scale.
  3) The BMP not only has effect on a bone tissue, but also affect other cells and organs. A wrong giving may cause calcification of tissues that cannot be ossified, such as adjacent muscles, nerves and blood vessels.
  4) It is necessary to directly and continuously give on a needed part due to a relatively short half-life period of the BMP.
  5) For greater bony defect, the BMP cannot serve as a stand, as a result, a proper carrier material is needed to cooperate with the BMP.

If the BMP can be combined with a proper carrier, consumption of the BMP may be greatly reduced, and the BMP can be limited to play a role on the special defect part, so that diffusion and ectopic osteogenesis are avoided, and the BMP is safer. As a result, it is necessary to research a slow-release system that can continuously release the BMP.

At present, materials for manufacturing the slow-release system mainly include a natural carrier, a synthesized biodegradable material and other inorganic substances, and the like. The natural carrier may be collagen, demineralized bone matrix (DBM), chitosan and the like. The materials have the advantages of good biocompatibility and biodegradation, which may be improved. The disadvantages of the materials are that diseases are possibly propagated in a material taking and processing process and immunogenicity exists as a result of a natural source. Compared with synthesized polymers, the materials are complex in structure, complex in professional production, and may cause difference in matrix consistency as a result of multi-time processing. In addition, the collagen and the BMP are poor in affinity, and the loaded BMP is completely released within two weeks in an implant. Besides, the polymers are lack of mechanical strength and cannot tolerate pressure. The synthesized biodegradable materials may be poly-lactic acid (PLA), PGA and a polymer thereof (poly-lactide-co-glycolide, PLGA), and the like. These materials are rich in source, can be processed into various shapes, are lack of osteoconductive property in comparison with allogenic bone transplantation, and have hydrophobicity. In addition, the pH value will be reduced by degradation products.

As a result, it is the main challenge in clinical research of constructing a bone morphogenetic protein slow-release system which is more stable, safer and better in economic efficiency to overcome the disadvantages of the carrier material.

BRIEF SUMMARY OF THE INVENTION

To solve the defects in the prior art, the present invention provides a method for constructing a bone morphogenetic protein slow-release system. Biological macromolecule polysaccharide, polypeptide and hydroxyapatite having good affinity with the BMP are organically combined to an integrally constructed bionic multilayer film through a layer-by-layer assembly method, and the BMP is loaded on the multilayer layer, so that construction of the bone morphogenetic protein slow-release system is achieved. The method has the advantages of being long-acting, stable, safe and economical, is gentle in process condition and is wide in applicable base material range.

According to the technical solution adopted in the present invention, a titanium material is taken as a base material for constructing a bone morphogenetic protein slow-release system,
  including the following steps:
  I: activating a titanium material: washing and drying the titanium material, soaking the dried titanium material into a buffer solution containing dopamine, and reacting for 12-72 hours to obtain a polydopamine (PDA)-modified Ti base material;
  II: activating ceramic powder: dissolving the ceramic powder and the dopamine into the buffer solution, vibrating and dispersing, reacting for 12-72 hours under stirring, and centrifuging to remove large particles, thereby obtaining a polydopamine-modified ceramic particles (PDA@HA) solution;
  III: constructing a multilayer film: sequentially soaking the PDA-modified Ti base material in a positively-charged polyelectrolyte solution, a negatively-charged polyelectrolyte solution, a positively-charged polyelectrolyte solution and the PDA@HA solution for 8-15 min, and washing with water after soaking; and
  IV: soaking in a circulating mode: soaking and cleaning in step III by circulating operation with circulating times of n times, thereby obtaining a positively-charged polyelectrolyte, negatively-charged polyelectrolyte and PDA-modified ceramic particles [(+/−/+/PDA@HA)$_n$] multilayer film.

The preparation method can be further optimized for strengthening the (+/−/+/PDA@HA)$_n$ multilayer film. The (+/−/+/PDA@HA)$_n$ multilayer film is soaked in a cross-linking solution for 6-24 hours, then washed with water and dried to obtain a cross-linked multilayer film which is recorded as a x(+/−/+/PDA@HA)$_n$ multilayer film.

Preferably, the buffer solution containing dopamine in step I is a Tris-HCl buffer solution with a dopamine concentration of 0.3-5.0 mg/mL, and a pH value of 8-9.

Preferably, the ceramic powder in step II is any one of hydroxyapatite, bioactive glass, calcium phosphate, aluminum oxide or zirconium oxide, and a weight ratio of the ceramic powder to the dopamine is (8-15) to 1.

Preferably, the positively-charged polyelectrolyte solution in step III is any one of a chitosan solution or a polylysine solution, with a concentration of 0.3-5.0 mg/mL; and/or, the negatively-charged polyelectrolyte solution is any one of a glucan solution, a heparin solution, a heparan sulfate solution, an alginic acid solution, a hyaluronic acid solution, a collagen solution, a gelatin solution, a carrageenan solution or a cellulose acetate solution, with a concentration of 0.3-5.0 mg/mL; and/or, the PDA@HA solution is a solution with a PDA@HA concentration of 0.3-5.0 mg/mL.

Preferably, the circulating times are greater than 3.

Preferably, the cross-linking solution is at least one of a carbodiimide solution with a concentration of 25-70 mg/mL, a thiosuccimide solution with a concentration of 5-25 mg/mL, a glutaraldehyde solution with a mass concentration of 2.5% or a genipin solution with a mass concentration of 1-4%.

The present invention further discloses a protein slow-release system which is characterized by being the bone morphogenetic protein slow-release system prepared according to any of the construction methods.

The invention further discloses a construction method of the bone morphogenetic protein loaded slow-release system, which is characterized by including: soaking the bone morphogenetic protein slow-release system into a solution containing the bone morphogenetic protein to load; or directly dropwise adding the solution containing the bone morphogenetic protein onto the bone morphogenetic protein slow-release system.

The present invention further discloses a bone morphogenetic protein loaded slow-release system which is characterized by being the bone morphogenetic protein loaded slow-release system prepared according to any of the construction methods.

The present invention has the following beneficial effects:

To solve the problem that an excellent carrier material is absent in a storage and use process of the bone morphogenetic protein, based on self-polymerization universality of dopamine, the positively-charged polyelectrolyte, for example chitosan (Chi) or polylysine, the negatively-charged polyelectrolyte, for example, glucan, heparin, heparan sulfate, alginic acid, hyaluronic acid (Ha), collagen, gelatin, carrageenan or cellulose acetate, ceramic powder with biological activity, for example hydroxyapatite (HA), bioactive glass, calcium phosphate, aluminum oxide or zirconium oxide are integrated onto the titanium base material in a layer-by-layer assembly mode to construct a bone morphogenetic protein slow-release system, so that long-acting slow release, on a lesion part, of the bone morphogenetic protein is achieved. The slow-release system has the advantages of being high in surface modulus, stable, resistant to radiation, good in biocompatibility, and the like, can effectively promote osteogenic differentiation of the mesenchymal stem cells, and can be expected to effectively promote bone repair.

While taking titanium as a substrate material, the titanium material is activated through self-polymerization characteristic, similar to mussel adhesive protein, on the substrate material, by dopamine. The titanium material which is activated through the dopamine can provide an active site for follow-up riveting of the multilayer film. The multilayer film is introduced, and the film layer mainly consists of positively-charged polyelectrolyte, negatively-charged polyelectrolyte and PDA-modified ceramic particles. The film layer is a (+/−/+/PDA@HA)$_n$ multilayer film, where n is circulating times of the four-layer film.

The specific type of the film layer materials is specifically limited in the present invention. Preferably, the multilayer film obtained by circulating the positively-charged chitosan (Chi), negatively-charged hyaluronic acid (Ha) and hydroxyapatite (HA) with biological activity for n times is recorded as a (Chi/Ha/Chi/PDA@HA)$_n$ multilayer film. Hydroxyapatite (HA) can provide a $Ca^{2+}$ ion source for in-vivo new bone generation, so that adhesion and proliferation as well as osteogenic differentiation of osteoblasts and pre-osteoblasts are promoted.

To solve the defects of being liable to agglomeration in water and poor in dispersion of hydroxyapatite, a dopamine self-polymerization technology is adopted for surface modification to improve the dispersion. After being modified, the hydroxyapatite is reduced in apparent size and greatly increased in dispersion in water. Due to the presence of polydopamine on the surface, hydroxyapatite particles can be combined with amino, so that PDA@HA can be participated in layer-by-layer assembly of the polyelectrolyte with amino. In addition, Young's modulus of the multilayer film surface can be greatly increased after hydroxyapatite is introduced into the multilayer film. Furthermore, the assembled multilayer film is chemically cross-linked, so that stability of the multilayer film can be further improved. A cross-linking agent also has positive influence on surface modulus of the multilayer film.

It is of great significance in increasing surface modulus. Generally, materials adaptive to different cells are different in hardness, nerve cells are suitable for being propagated and differentiated on softer materials, and osteoblasts prefer harder materials. The bone morphogenetic protein involved in the present invention is mainly used to bone cell related fields. The increase of the surface modulus is beneficial for spread, proliferation and differentiation of the cells. The modus on the surface of the multilayer is strengthened to promote adhesion and proliferation as well as osteogenic differentiation of the osteoblasts and the pre-osteoblasts. As a result, a good physical and chemical micro environment is provided for generation of new bones on the surface of implant.

Then, the BMP is successfully loaded through a rear diffusion method, in-vitro slow release of the BMP is reduced due to cross-linking of the multilayer film, so that long-acting slow release of the lesion part is achieved. In addition, the multilayer film has obvious protecting effect on osteoblast proliferation. After the BMP is loaded, osteogenic differentiation of the mesenchymal stem cells can be remarkably induced. In addition, the multilayer film has a good protection effect on the loaded BMP. BMP-2 still has about 70% of the activity after being sterilized through a γ-ray according to in-vitro cell ALP detection. The in-vivo experiment assessment results show that the BMP-2 keeps most of biological activity.

In conclusion, three different film layers in the multilayer film are mutually matched: proliferation and intercellular fusion of the mesenchymal stem cells can be greatly improved through good biocompatibility of natural polysaccharide, good affinity on the osteoblasts of hydroxyapatite and promotion effect, on osteogenesis, of long-acting slow release of the loaded bone morphogenetic protein, so that bone repair is effectively promoted. Meanwhile, the method also can be expanded to loading and protection of other protein drugs.

BRIEF DESCRIPTION OF THE DRAWINGS

The present invention is further illustrated in combination with the accompanying drawings hereinafter.

DETAILED DESCRIPTION OF THE INVENTION

Figure 1:
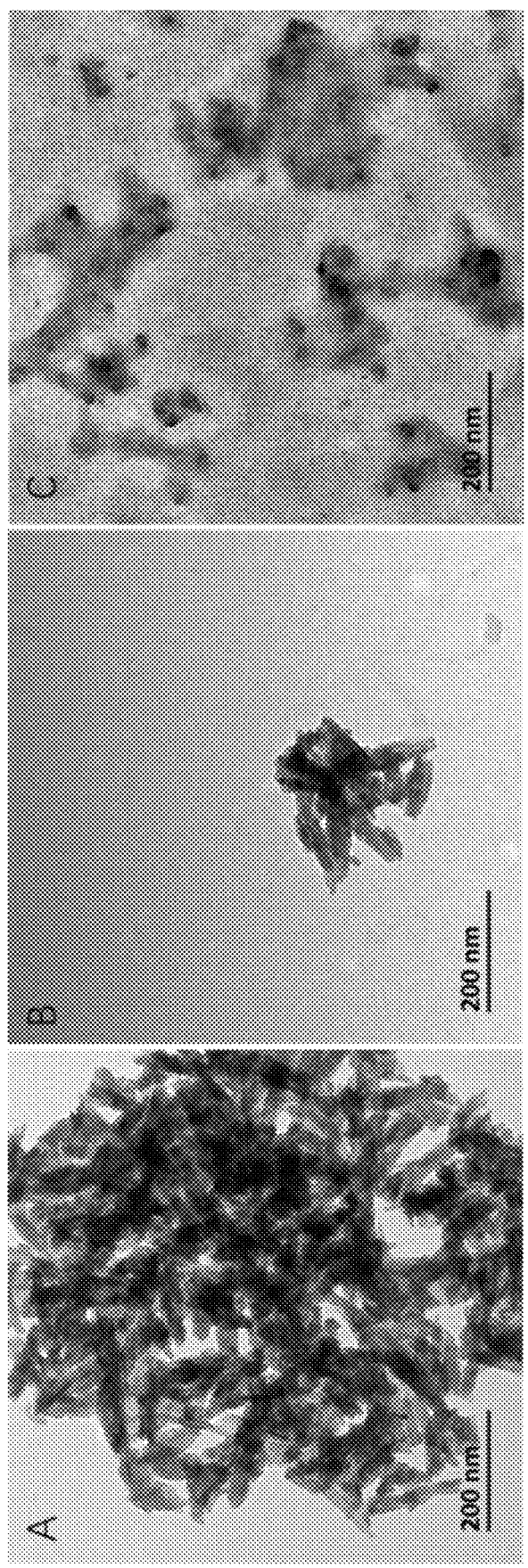
FIG. 1 is a transmission electron microscope micrograph of hydroxyapatite: A) unmodified hydroxyapatite, B) hydroxyapatite modified with dopamine, C) dopamine self-polymer, where dopamine self-polymer particles can be visibly small.
Figure 2:
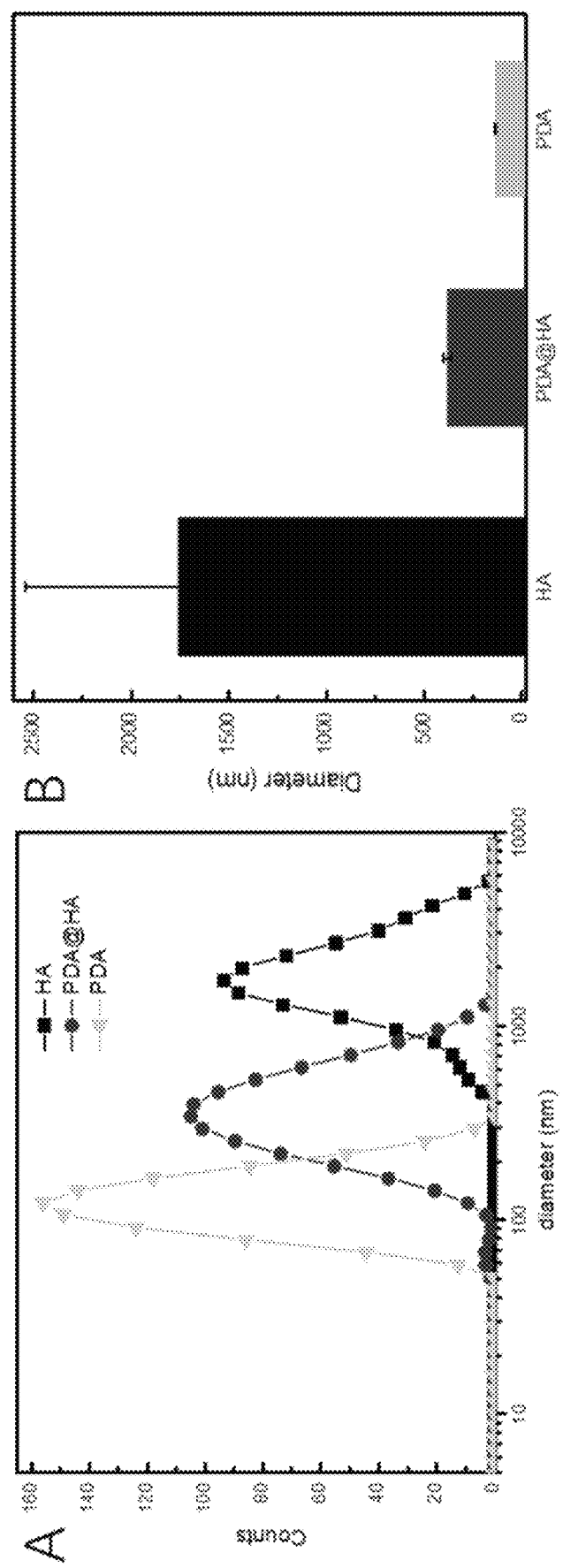
FIG. 2 shows results of dynamic light scattering detection of a hydroxyapatite grain size: A) a grain size distribution diagram of hydroxyapatite and dopamine self-polymer un-modified and modified with dopamine, B) an average grain size histogram of hydroxyapatite and dopamine self-polymer un-modified and modified with dopamine.
Figure 3:
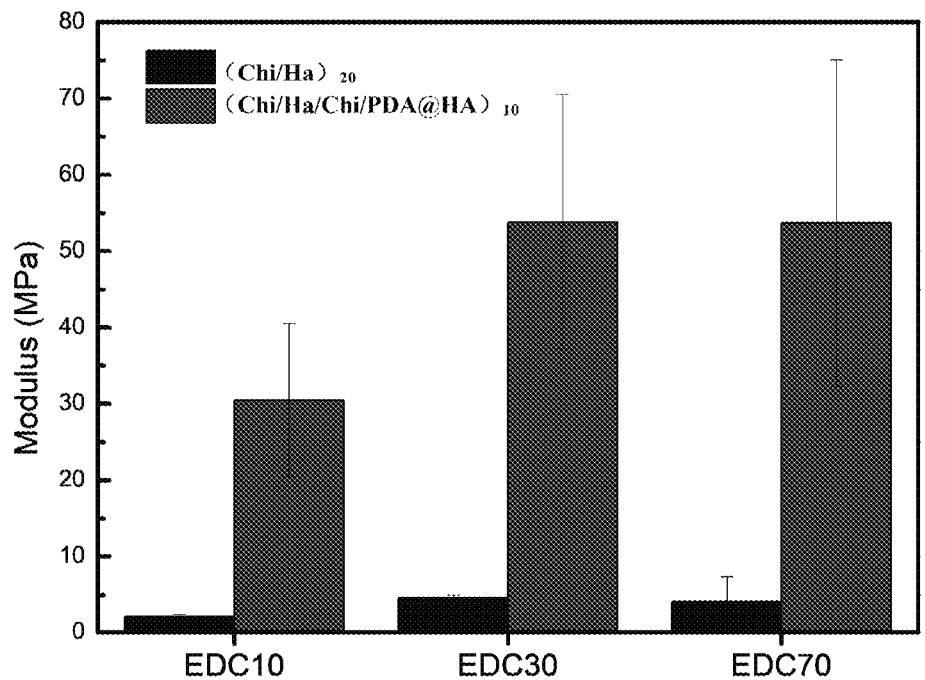
FIG. 3 shows surface modulus, measured by a nano indentor, of a (Chi/Ha)$_{20}$ multilayer film and a (Chi/Ha/Chi/PDA@HA)$_{10}$ multilayer film. Longitudinal coordinates are Young's modulus values, and horizontal ordinates are concentrations of the cross-linking agent EDC, which are 10 mg/mL, 30 mg/mL and 70 mg/mL respectively.
Figure 4:
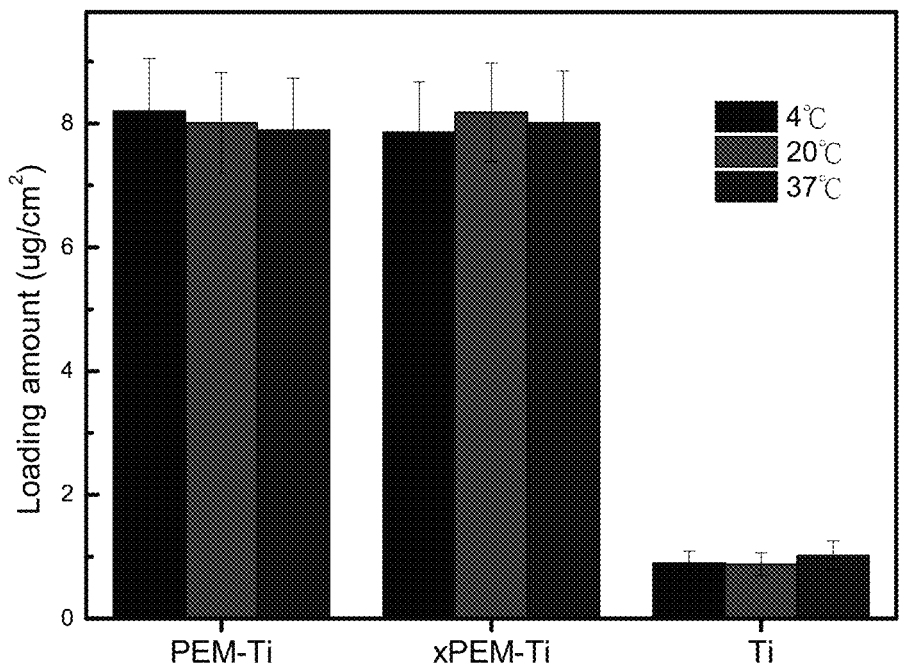
FIG. 4 is BMP-2 loading amount, at different temperatures, of a titanium surface modified with the (Chi/Ha/Chi/PDA@HA)$_{10}$ multilayer film: longitudinal coordinates are loading amount of BMP-2, PEM-Ti is the titanium surface modified with the (Chi/Ha/Chi/PDA@HA)$_{10}$ multilayer film, xPEM-Ti is a titanium surface modified with the cross-linked (Chi/Ha/Chi/PDA@HA)$_{10}$ multilayer film, and Ti is an unmodified titanium surface.

The present invention is further illustrated in combination with the specifically embodiments hereinafter.

Embodiment 1

Step I: a titanium material was activated. The titanium material was washed and dried, and then was soaked into a Tris-HCl buffer solution containing dopamine with a concentration of 1 mg/mL and a pH value of 8.5 to react for 48 hours to obtain a PDA-modified Ti base material.

Step II: ceramic powder is activated. The ceramic powder and dopamine were weighed in a weight ratio of 10:1, were dissolved into the Tris-HCl buffer solution, were vibrated for several minutes in an ultrasonic pulverizer to disperse ceramic particles, were reacted for 48 hours under stirring, and were centrifuged to remove large particles, so that a PDA@HA solution was obtained.

Step III: a multilayer film was constructed. The PAD-modified Ti base material was sequentially soaked in a solution with a chitosan concentration of 1 mg/mL, a solution with a hyaluronic acid concentration of 1 mg/mL, a solution with a chitosan concentration of 1 mg/mL and a solution with a PDA@HA concentration of 1 mg/mL for 10 min every time, and then was cleaned with water.

Step IV: the base material was soaked in a circulating mode: the base material was soaked and cleaned for 10 times in step III to obtain a (Chi/Ha/Chi/PDA@HA)$_{10}$ multilayer film which was recorded as Ti+PEM.

Embodiment 2

Further, (Chi/Ha/Chi/PDA@HA)$_{10}$ multilayer film obtained in Embodiment 1 was strengthened and was soaked into a cross-linking solution containing carbodiimide (EDC) and thiosuccimide (sNHS) to stay overnight, where the concentration of the EDC was 30 mg/mL, and the concentration of the sNHS was 11 mg/mL. Then, the multilayer film was sufficiently washed with water and dried to obtain a cross-linked (Chi/Ha/Chi/PDA@HA)$_{10}$ multilayer film.

Embodiment 3

Further, the cross-linked (Chi/Ha/Chi/PDA@HA)$_{10}$ multilayer film obtained in Embodiment 2 was loaded with the bone morphogenetic protein as follows: the crossed-linked (Chi/Ha/Chi/PDA@HA)$_{10}$ multilayer film was soaked into a bone morphogenetic protein-2 (BMP-2) solution with a concentration of 20 ug/mL and a pH value of 3.0 to load to finally obtain a slow-release system loaded with the BMP-2: Ti+PEM+BMP-2.

Embodiment 4

Further, the (Chi/Ha/Chi/PDA@HA)$_{10}$ multilayer film obtained in Embodiment 1 was strengthened and was soaked into a cross-linking solution containing glutaraldehyde with a mass concentration of 2.5% and genipin with a mass concentration of 3% to stay overnight. Then, the multilayer film was sufficiently washed with water and dried to obtain a cross-linked (Chi/Ha/Chi/PDA@HA)$_{10}$ multilayer film.

Embodiment 5

Further, the cross-linked (Chi/Ha/Chi/PDA@HA)$_{10}$ multilayer film obtained in Embodiment 4 was loaded with the bone morphogenetic protein as follows: the crossed-linked (Chi/Ha/Chi/PDA@HA)$_{10}$ multilayer film was soaked into a bone morphogenetic protein-2 (BMP-2) solution with a concentration of 20 ug/mL and a pH value of 3.0 to load to finally obtain a slow-release system loaded with the BMP-2: Ti+PEM+BMP-2.

Embodiment 6

Further, the (Chi/Ha/Chi/PDA@HA)$_{10}$ multilayer film obtained in Embodiment 1 was strengthened and soaked into a cross-linking solution containing EDC with a mass concentration of 30 mg/mL to stay overnight. Then, the multilayer film was sufficiently washed with water and dried to obtain a cross-linked (Chi/Ha/Chi/PDA@HA)$_{10}$ multilayer film.

Embodiment 7

Further, the (Chi/Ha/Chi/PDA@HA)$_{10}$ multilayer film obtained in Embodiment 1 was strengthened and soaked into a cross-linking solution containing sNHS with a mass concentration of 11 mg/mL to stay overnight. Then, the multilayer film was sufficiently washed with water and dried to obtain a cross-linked (Chi/Ha/Chi/PDA@HA)$_{10}$ multilayer film.

Embodiment 8

Further, the (Chi/Ha/Chi/PDA@HA)$_{10}$ multilayer film obtained in Embodiment 1 was strengthened and soaked into a cross-linking solution containing glutaraldehyde with a mass concentration of 2.5% to stay overnight. Then, the multilayer film was sufficiently washed with water and dried to obtain a cross-linked (Chi/Ha/Chi/PDA@HA)$_{10}$ multilayer film.

Embodiment 9

Further, the (Chi/Ha/Chi/PDA@HA)$_{10}$ multilayer film obtained in Embodiment 1 was strengthened and soaked into a cross-linking solution containing genipin with a mass concentration of 3% to stay overnight. Then, the multilayer film was sufficiently washed with water and dried to obtain a cross-linked (Chi/Ha/Chi/PDA@HA)$_{10}$ multilayer film.

Comparative Example 1

The cross-linking solution used in step V included EDC with a mass concentration of 10 mg/mL and sNHS with a mass concentration of 11 mg/mL.

Other operations were the same with those in Embodiment 2.

Comparative Example 2

The cross-linking solution used in step V included EDC with a mass concentration of 70 mg/mL and sNHS with a mass concentration of 11 mg/mL.

Other operations were the same with those in Embodiment 2.

Comparative Example 3

Step I: a titanium material was activated. The titanium material was washed and dried, and then was soaked into a Tris-HCl buffer solution containing dopamine with a concentration of 1 mg/mL and a pH value of 8.5 to react for 48 hours to obtain a PDA-modified Ti base material.

Step II: ceramic powder is activated. The ceramic powder and dopamine were weighed in a weight ratio of 10:1, were dissolved into the Tris-HCl buffer solution, were vibrated for several minutes in an ultrasonic pulverizer to disperse ceramic particles, were reacted for 48 hours under stirring, and were centrifuged to remove large particles, so that a PDA@HA solution was obtained.

Step III: a multilayer film was constructed. The PAD-modified Ti base material was sequentially soaked in a solution with a chitosan concentration of 1 mg/mL and a pH value of 4.0 and a solution with a hyaluronic acid concentration of 1 mg/mL and a pH value of 4.0 for 10 min every time, and then was cleaned with water.

Step IV: the base material was soaked in a circulating mode: the base material was soaked and cleaned for 20 times in step III to obtain a (Chi/Ha)$_{20}$ multilayer film.

Step V: strengthening aftertreatment was performed. The (Chi/Ha)$_{20}$ multilayer film obtained was soaked into a cross-linking solution containing carbodiimide (EDC) and thiosuccimide (sNHS) to stay overnight, where the concentration of the EDC was 30 mg/mL, and the concentration of the sNHS was 11 mg/mL. Then, the multilayer film was sufficiently washed with water and dried to obtain a cross-linked (Chi/Ha)$_{20}$ multilayer film.

Comparative Example 4

The cross-linking solution used in step V included EDC with a mass concentration of 10 mg/mL and sNHS with a mass concentration of 11 mg/mL.

Other operations were the same with those in Comparative Example 3.

Comparative Example 5

The cross-linking solution used in step V included EDC with a mass concentration of 70 mg/mL and sNHS with a mass concentration of 11 mg/mL.

Other operations were the same with those in Comparative Example 3.

Comparative Example 6

According to a method of loading the BMP-2 protein in Embodiment 3, the BMP-2 was directly loaded onto Ti+PEM which was not cross-linked, where the preparation method of Ti+PEM was the same in Embodiment 1.

Comparative Example 7

According to a method of loading the BMP-2 protein in Embodiment 3, the BMP-2 was directly loaded onto the titanium material (Ti), where the pretreatment (washing and drying) of Ti was the same in Embodiment 1.

Comparative Example 8

The titanium material (Ti) which was only washed and dried was provided.

TABLE 1

Comparative Table between Embodiments 1-9 and Comparative Examples 1-8

| Items | Composition of multilayer film | Cross-linked or not |
|---|---|---|
| Embodiment 1: | (Chi/Ha/Chi/PDA@HA)$_{10}$ | Ti + PEM (not cross-linked) |
| Embodiment 2: | (Chi/Ha/Chi/PDA@HA)$_{10}$ | Ti + PEM (cross-linked) |
| Embodiment 3: | (Chi/Ha/Chi/PDA@HA)$_{10}$ | Ti + PEM BMP-2 (cross-linked) |
| Embodiment 4: | (Chi/Ha/Chi/PDA@HA)$_{10}$ | Ti + PEM (cross-linked) |
| Embodiment 5: | (Chi/Ha/Chi/PDA@HA)$_{10}$ | Ti + PEM BMP-2 (cross-linked) |
| Embodiment 6: | (Chi/Ha/Chi/PDA@HA)$_{10}$ | Ti + PEM (cross-linked) |
| Embodiment 7: | (Chi/Ha/Chi/PDA@HA)$_{10}$ | Ti + PEM BMP-2 (cross-linked) |
| Embodiment 8: | (Chi/Ha/Chi/PDA@HA)$_{10}$ | Ti + PEM (cross-linked) |
| Embodiment 9: | (Chi/Ha/Chi/PDA@HA)$_{10}$ | Ti + PEM BMP-2 (cross-linked) |
| Comparative Example 1 | (Chi/Ha/Chi/PDA@HA)$_{10}$ | Ti + PEM (cross-linked) |
| Comparative Example 2 | (Chi/Ha/Chi/PDA@HA)$_{10}$ | Ti + PEM (cross-linked) |
| Comparative Example 3 | (Chi/Ha)$_{20}$ | Ti + (Chi/Ha)20 (cross-linked) |
| Comparative Example 4 | (Chi/Ha)$_{20}$ | Ti + (Chi/Ha)20 (cross-linked) |
| Comparative Example 5 | (Chi/Ha)$_{20}$ | Ti + (Chi/Ha)20 (cross-linked) |
| Comparative Example 6 | (Chi/Ha/Chi/PDA@HA)$_{10}$ | Ti + PEM BMP-2 (not cross-linked) |
| Comparative Example 7 | — | Ti-BMP-2 |
| Comparative Example 8 | — | Ti |

Then, slow-release behaviors and related properties of the slow-release system obtained in each Embodiment and Comparative Example were tested and represented.

Surface properties and mechanical properties of the obtained material were tested through a transmission electron microscope, dynamic light scattering, a scanning electron microscope, a nano indentor and the like.

The multilayer film loaded with the BMP-2 was soaked into 37° C. PBS, and in-vitro release behaviors of a protein body were detected by detecting the concentration of BMP-2 in the soaking PBS solution at intervals.

Then, an adhesion proliferation of osteoblasts on the surface of the multilayer film was detected through a CCK-8 kit and a dyeing experiment; and promotion on osteogenic differentiation of mesenchymal stem cells was evaluated based on a BMP-2 slow-release system of the multilayer film through a western blotting test.

According to an anti-radiation test, γ-ray irradiation was directly performed on each product, and SEM surface topography and osteogenic induction activity before and after γ-ray irradiation were detected, and finally the multilayer film was assembled onto a porous titanium cylindrical bracket through a rat intervertebral fusion model to inspect promotion effect, on intervertebral fusion, of the bracket.

Figure 7:
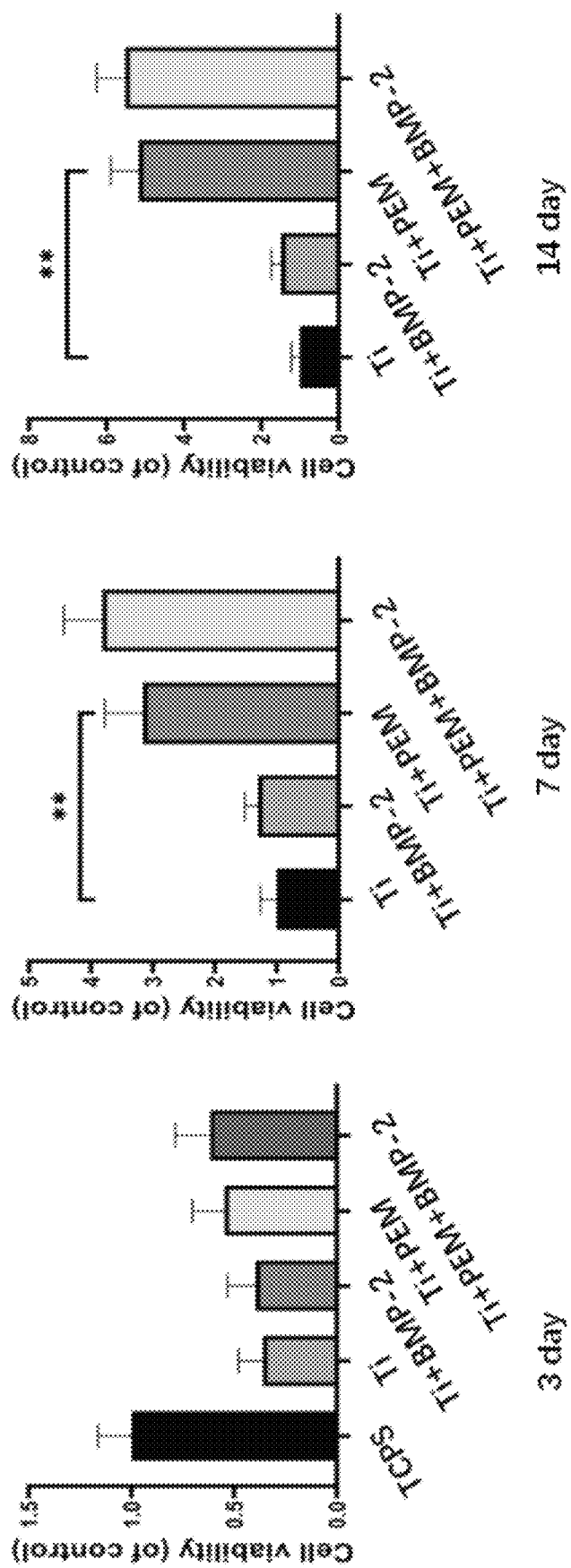
FIG. 7 shows activity and a proliferation condition, detected by CCK-8, of osteoblasts.
Figure 8:
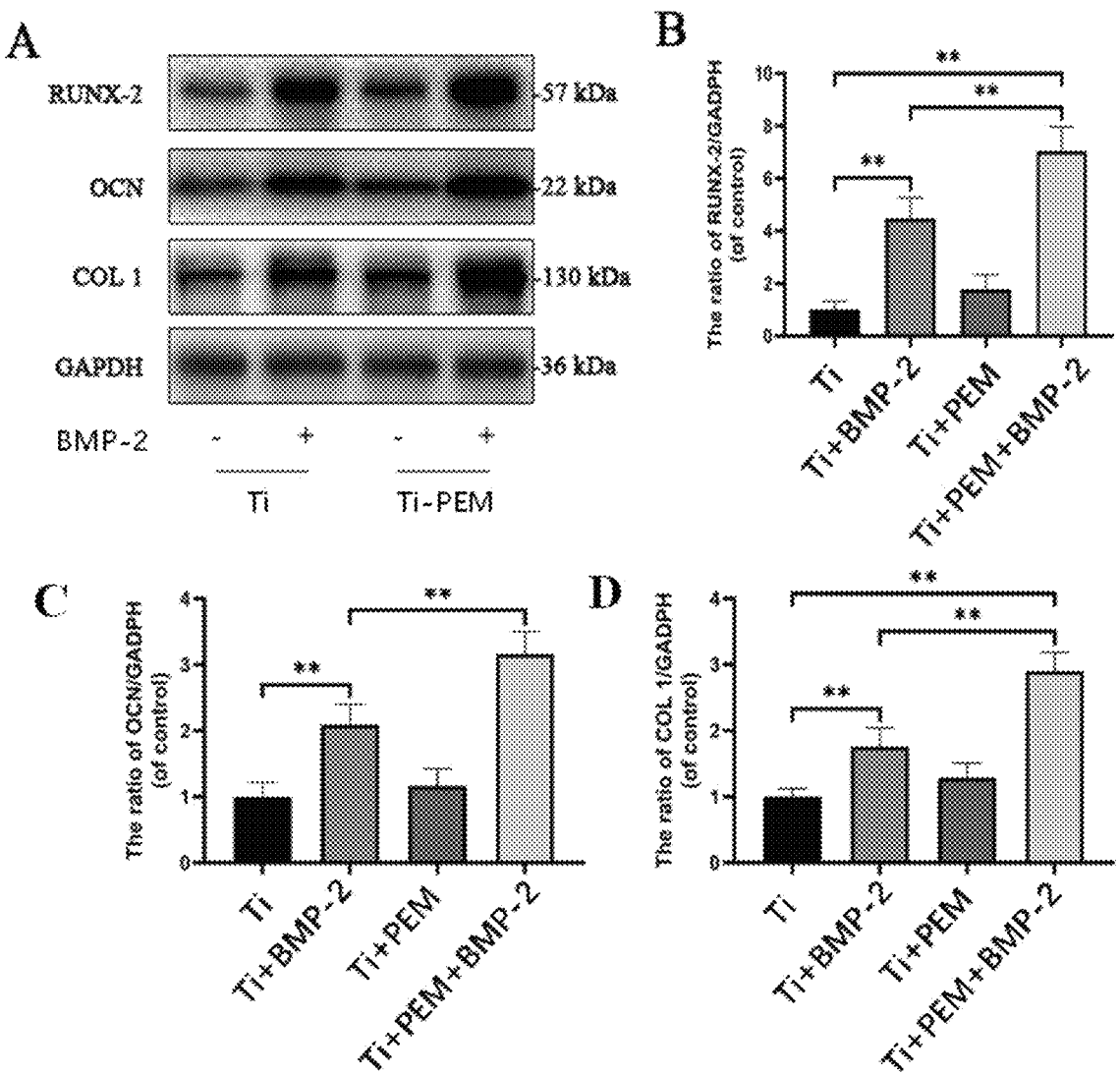
FIG. 8 shows western blot results on a functional mechanism after mesenchymal stem cells are cultured for 14 days on different base material surfaces: A) a representative WB stripe; B-D), RUNX-2, OCN and COL 1 quantitative results.

See FIG. 1 to FIG. 13 for the detected results, and from FIG. 8, "Ti+PEM" was a titanium surface modified with the cross-linked (Chi/Ha/Chi/PDA@HA) 10 multilayer film.

The titanium material was selected as a substrate material, and was activated through self-polymerization characteristic, on the substrate material, of dopamine similar to the mussel adhesive protein; then, the multilayer film which mainly consisted of chitosan (Chi), hyaluronic acid (Ha) and PDA-modified hydroxyapatite (HA) was then introduced, and the structure of the film layer was the (Chi/Ha/Chi/PDA@HA)$_n$ multilayer film, where n was circulating times of the four-layer film. The hyaluronic acid (Ha) was polyanion, the chitosan (Chi) was polycation and the hydroxyapatite could provide a $Ca^{2+}$ ion source for in-vivo new bone generation, so that adhesion proliferation and osteogenic differentiation of osteoblasts and pre-osteoblasts were promoted. Three different film layers in the multilayer film were mutually matched: proliferation and intercellular fusion of the mesenchymal stem cells could be greatly improved through good biocompatibility of natural polysaccharide, good affinity on the osteoblasts of hydroxyapatite and promotion effect, on osteogenesis, of long-acting slow release of the loaded bone morphogenetic protein.

However, to solve the defects of being liable to agglomeration in water and poor in dispersion of hydroxyapatite, a dopamine self-polymerization technology was adopted for surface modification to improve the dispersion. After being modified, the hydroxyapatite was strengthened in dispersion and reduced in apparent size (refer to FIG. 1). More specifically, refer to FIG. 2, the apparent size of the hydroxyapatite (HA), the dopamine-modified nano-hydroxyapatite (PDA@HA) and dopamine self-polymer (PDA) was detected through dynamic light scattering. The dispersion, in water, of the dopamine-modified nano-hydroxyapatite was greatly improved as the agglomeration apparent size, in water, of the hydroxyapatite was 1.759 microns, and the apparent size was reduced to be 381.8 nanometers. Dopamine was self-polymerized under the same conditions to obtain a particle size of about 133.4 nanometers. Visibly, the dispersion, in water, of the nano-hydroxyapatite was greatly improved through modification of dopamine. Due to the presence of polydopamine on the surface, nano particles could be combined with amino, so that PDA@HA could be participated in layer-by-layer assembly of the polyelectrolyte with amino. In addition, after the hydroxyapatite was introduced into the multilayer film, Young modulus of the surface of the multilayer film could be greatly improved, refer to FIG. 3. In addition, the assembled multilayer could be chemically cross-linked to further improve the stability of the multilayer film. The surface modulus of the multilayer film could be affected by concentration of a cross-linking agent.

It was of great significance in increasing surface modulus. Generally, materials adaptive to different cells were different in hardness, nerve cells were suitable for being propagated and differentiated on softer materials, and osteoblasts preferred harder materials. The bone morphogenetic protein involved in the present invention was mainly used to bone cell related fields. The increase of the surface modulus was beneficial for spread, proliferation and differentiation of the cells. The modus on the surface of the multilayer was strengthened to promote adhesion and proliferation as well as osteogenic differentiation of the osteoblasts and the pre-osteoblasts. As a result, a good physical and chemical micro environment was provided for generation of new bones on the surface of implant.

In addition, by comparing the Embodiment 2, the Comparative Example 6 and the Comparative Example 8, the unmodified titanium surface was relatively flat only with some cutting or polishing marks. The titanium surface modified with the (Chi/Ha/Chi/PDA@HA)$_{10}$ multilayer film (cross-linked and not cross-linked) was obviously granular with a grain size of about 200-300 nm. The loading amount of the bone morphogenetic protein on the titanium base material modified with the multilayer film was greatly increased, refer to FIG. 4. Visibly, the (Chi/Ha/Chi/PDA@HA)$_n$ multilayer film was a good loading platform of the bone morphogenetic protein.

Figure 5:
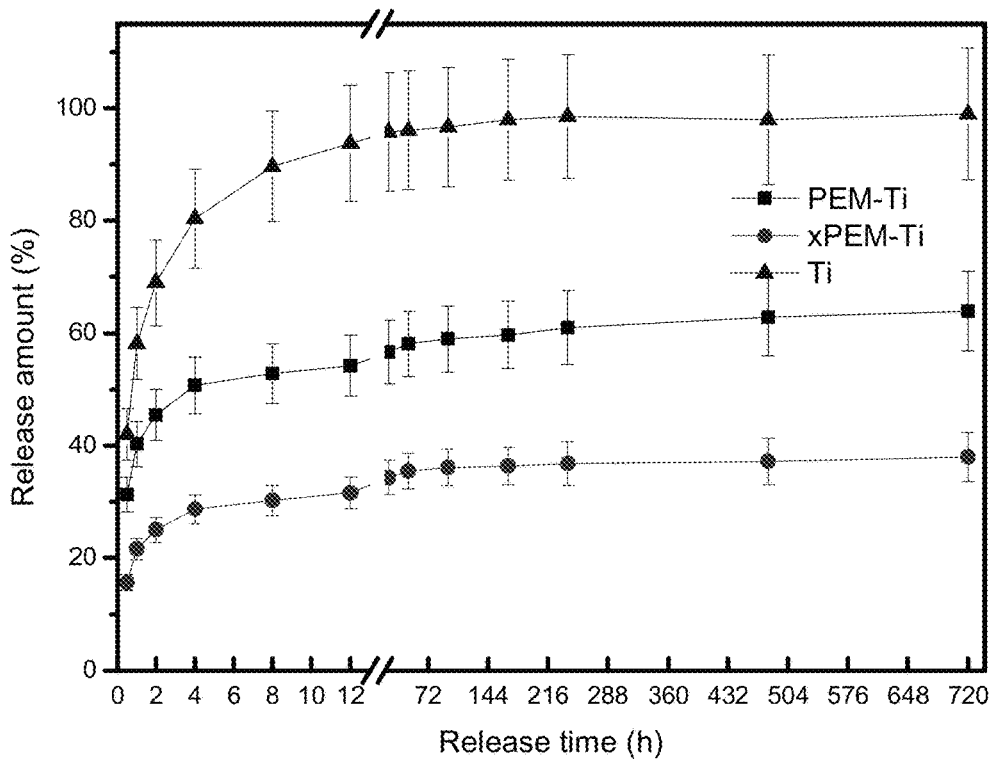
FIG. 5 shows an in-vitro slow-release condition (release percentage), on the loaded BMP-2, of the titanium surface modified with the (Chi/Ha/Chi/PDA@HA)$_{10}$ multilayer film: horizontal ordinates are slow-release time, longitudinal coordinates are release percentage, PEM-Ti is the titanium surface modified with the (Chi/Ha/Chi/PDA@HA)$_{10}$ multilayer film, xPEM-Ti is a titanium surface modified with the cross-linked (Chi/Ha/Chi/PDA@HA)$_{10}$ multilayer film, and Ti is an unmodified titanium surface.
Figure 6:
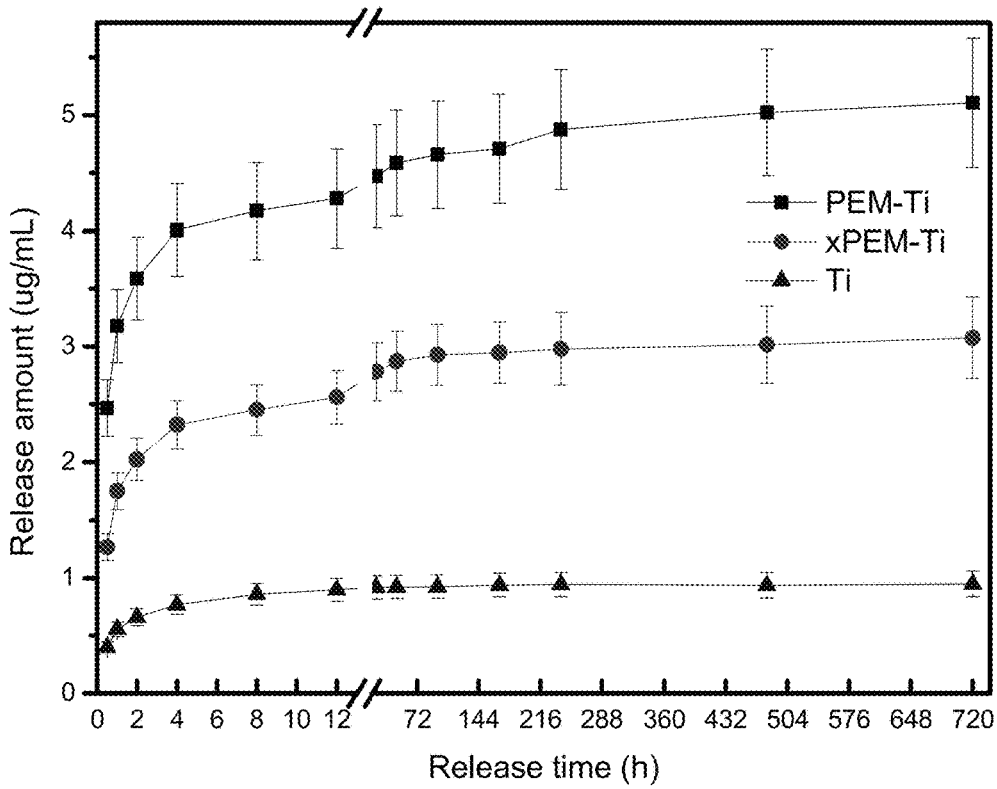
FIG. 6 shows an in-vitro slow-release condition (loading amount), on the loaded BMP-2, of the titanium surface modified with the (Chi/Ha/Chi/PDA@HA)$_{10}$ multilayer film: horizontal ordinates are slow-release time, longitudinal coordinates are release amount, PEM-Ti is the titanium surface modified with the (Chi/Ha/Chi/PDA@HA)$_{10}$ multilayer film, xPEM-Ti is a titanium surface modified with the cross-linked (Chi/Ha/Chi/PDA@HA)$_{10}$ multilayer film, and Ti is an unmodified titanium surface.

In-vitro slow-release experiment of the BMP-2 was performed in the PBS solution, and the results were seen in FIG. 5 and FIG. 6. Most of the BMP-2 on the unmodified titanium base material was released into the solution with the first several hours, and the integral release amount was smaller due to the very low loading amount. After the multilayer film which was not cross-linked was modified, release speed of the BMP-2 was obviously reduced, and more than 40% of the BMP-2 was still kept in the film after being released for one week, and therefore, concentration of the BMP-2 in the solution was greater; after the multilayer film was cross-linked, release speed of BMP-2 was further reduced, and about 30% of the BMP-2 was released into the solution one week later.

The stability of the cross-linked multilayer film was improved, the slow-release effect on the BMP-2 was better; and enough high BMP-2 concentration could be kept in the solution.

The evaluation results of the biocompatibility were as follows:

Cellular compatibility of the multilayer film was detected through in-vitro osteoblast culture, and cell activity and a proliferation condition were firstly detected through a CCK-8 kit. As shown in FIG. 7, an initial loading rate of the cells was higher than 50%, and cells on the surfaces of the multilayer film and the BMP-2 loaded on the multilayer film were obviously increased along with time. But in the Ti+BMP-2 group, burst release of the BMP-2 only occurred within the first several hours, so that influence on proliferation of the cells was not great. Further, the mesenchymal stem cells were seeded on the material surface, and were cultured for 14 days in an osteogenic induction culture medium, and the spreading morphology, on the material surface, of the mesenchymal stem cells was observed by dyeing cytoskeleton and cell nucleus. Only a few cells and cell aggregates were on an unmodified glass base material, and were slightly increased in the presence of BMP-2; coating, by the multilayer film, of the base material exhibited greater promotion effect on cell proliferation, so that a great number of aggregates were formed; and the multilayer film was further combined with the BMP-2, so that cell reproductive capacity on the surface of the BMP-2 slow-release material was further improved, and the formed cell aggregates were stacked into a grid. Visibly, proliferation and intercellular fusion of the mesenchymal stem cells could be greatly improved by combining good biocompatibility of natural polysaccharide, good affinity on the bone cells of hydroxyapatite and promotion effect, on osteogenesis, of long-acting slow release of the BMP-2.

The promotion effect, on osteogenic differentiation of the mesenchymal stem cells, of the BMP-2 slow-release system based on the multilayer film was evaluated through western blotting with results as shown in FIG. 8. Visibly, osteogenic differentiation indexes such as RUNX-2, OCN and COL 1 in the cells on Ti were obviously increased due to addition of the BMP-2 after the mesenchymal stem cells were cultured for 14 days in the osteogenic induction culture medium. Coating of the multilayer film exhibited obvious promotion effect (refer to FIG. 7) on cell proliferation, but the promotion effect on osteogenic differentiation was limited, and osteogenic differentiation indexes of the cells on the Ti-PEM+BMP-2 system were greatly strengthened. Visibly, the promotion effect, on cell proliferation, of the multilayer film and the lasting promotion effect, on osteogenic differentiation induction, of the slow-released BMP-2 were combined. The BMP-2 slow-release system based on the multilayer film in the study could effectively promote osteogenic differentiation of the mesenchymal stem cells, and could effectively promote bone repair as expected.

Further, influence on gamma-ray was detected:

Storage and sterilization of protein drugs had been a great bottleneck of restricting extensive use thereof. The protein drugs generally had specifically three-dimensional structures, and biological functionality of the proteins was generally from the three-dimensional structures. However, the three-dimensional structures were relatively weak, and it was the crucial problem to be solved of storing, especially keeping the structures and activity of the proteins in the sterilizing process in clinical application of the protein drugs. Protein inactivation would be caused as the structures of the proteins were damaged without doubt by direct heating and sterilizing as well as ethylene oxide sterilizing. In the study, the protection effect, on activity of the BMP-2 protein, of the multilayer film slow-release system was detected through gamma-ray irradiation sterilization. The slow-release system was sterilized by γ-ray irradiation through a Co60 source, and the radiation dose was 25 KGy.

Figure 9:
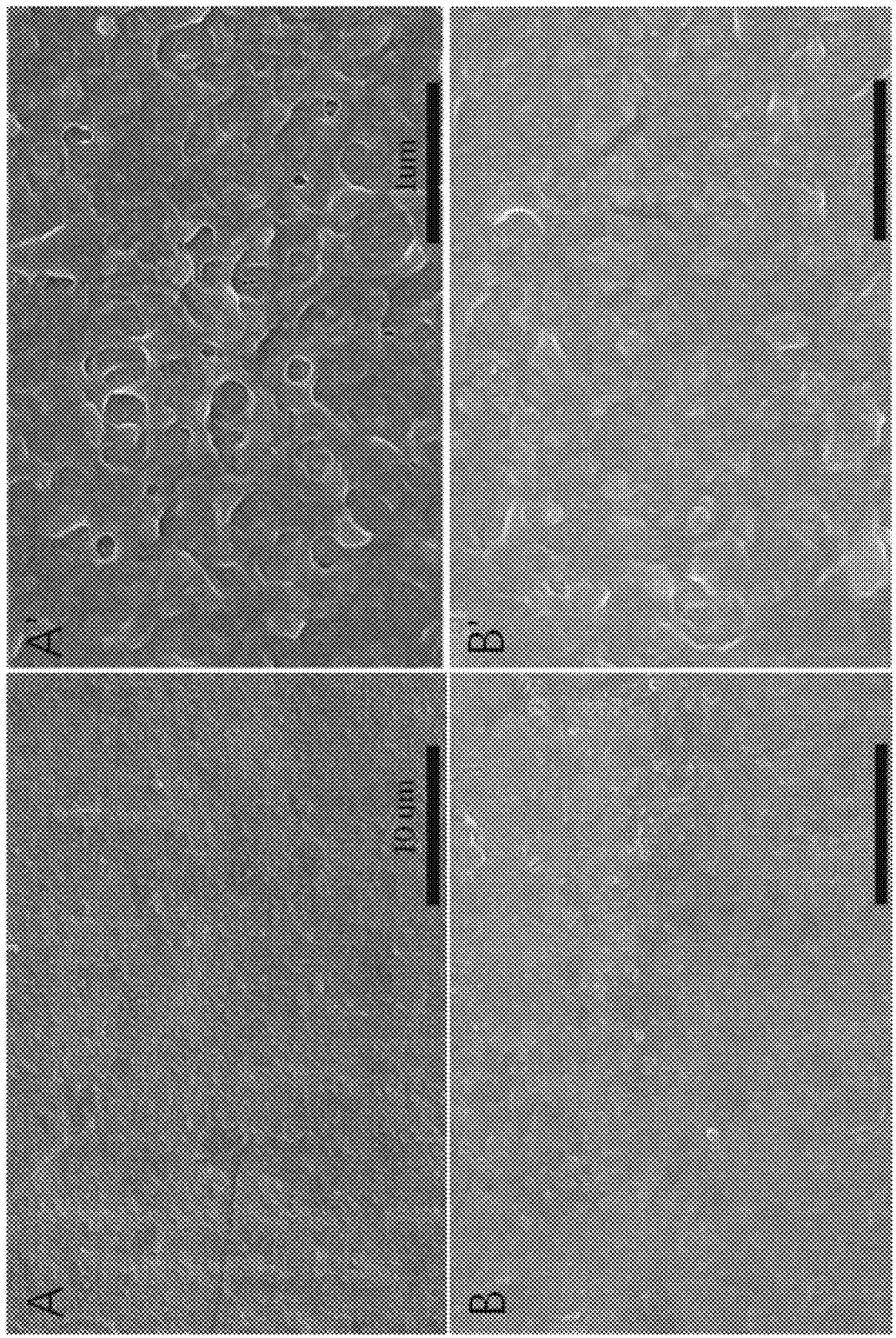
FIG. 9 is an SEM surface morphology of Ti+PEM+BMP-2 system before and after γ-ray sterilization: A, A') before sterilization, B, B') after sterilization.
Figure 10:
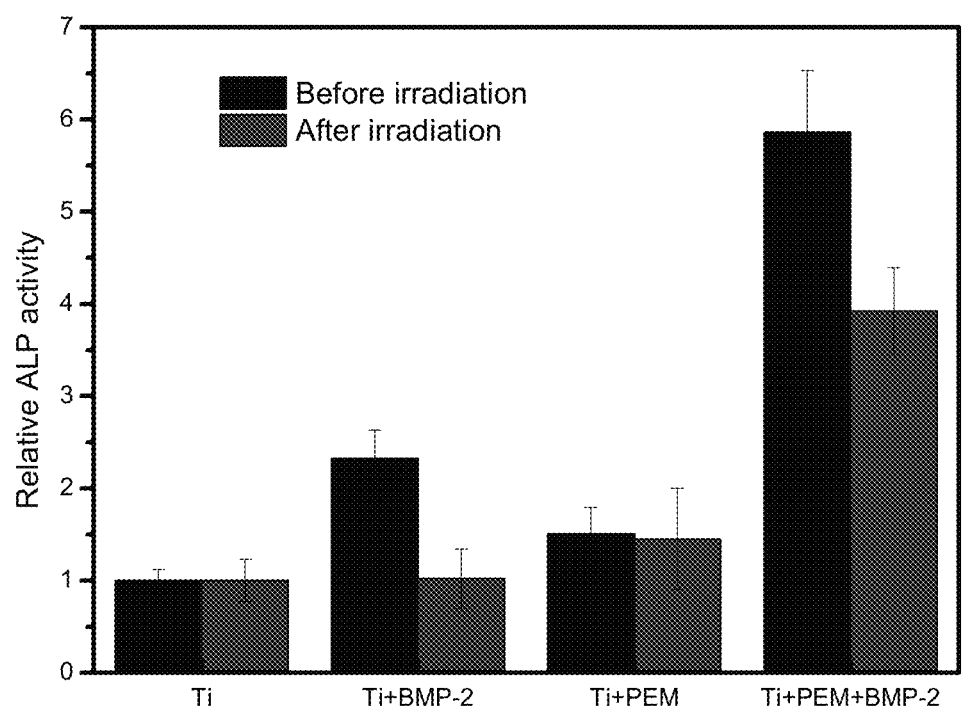
FIG. 10 shows ALP expression of bone marrow mesenchymal stem cells on the surface of a multilayer BMP-2 slow-release system before and after γ-ray irradiation sterilization (after 3 days of culture).

It could be seen from the FIG. 9 showing the surface topography of the multilayer film before and after irradiation sterilization that there were no obvious changes in surface topography of the multilayer film after gamma-ray irradiation sterilization.

To detect biological activity of the BMP-2 protein in the multilayer film after irradiation sterilization, the osteogenic differentiation condition on the surface of the multilayer film of the mesenchymal stem cells was quantified by measuring alkaline phosphatase (ALP). As shown in the FIG. 10, there were no obvious changes in ALP expression amount before and after base material sterilization of the BMP-2, and the BMP-2 was completely inactivated after the Ti+BMP-2 base material uncoated with the multilayer film was sterilized. However, the BMP-2 loaded in the multilayer slow-release system still kept most of biological activity after being sterilized. Visibly, the multilayer film not only could provide a carrier for the BMP-2 to achieve long-acting slow release on a lesion, but also could protect the protein from being damaged by radiation.

Finally, the evaluation results of the biocompatibility were as follows:

A rat intervertebral fusion model was selected for assembling the multilayer film onto a porous titanium cylindrical bracket to inspect promotion effect, on intervertebral fusion, of the bracket.

The porous titanium base material was rolled into a barrel, and was sequentially soaked into a hydroxyapatite (PDA@HA) solution modified with chitosan (Chi), hyaluronic acid (Ha), chitosan (Chi) and dopamine for 10 cycles to obtain a Ti+PEM bracket; further, the bracket was soaked into the BMP-2 solution with a concentration of 20 ug/mL to load the proteins, so that the Ti+PEM+BMP-2 bracket was obtained; and finally, the bracket was subjected to irradiation sterilization with sterilization dose of 25 KGy to obtain a γ-Ti+PEM+BMP-2 bracket.

Figure 11:
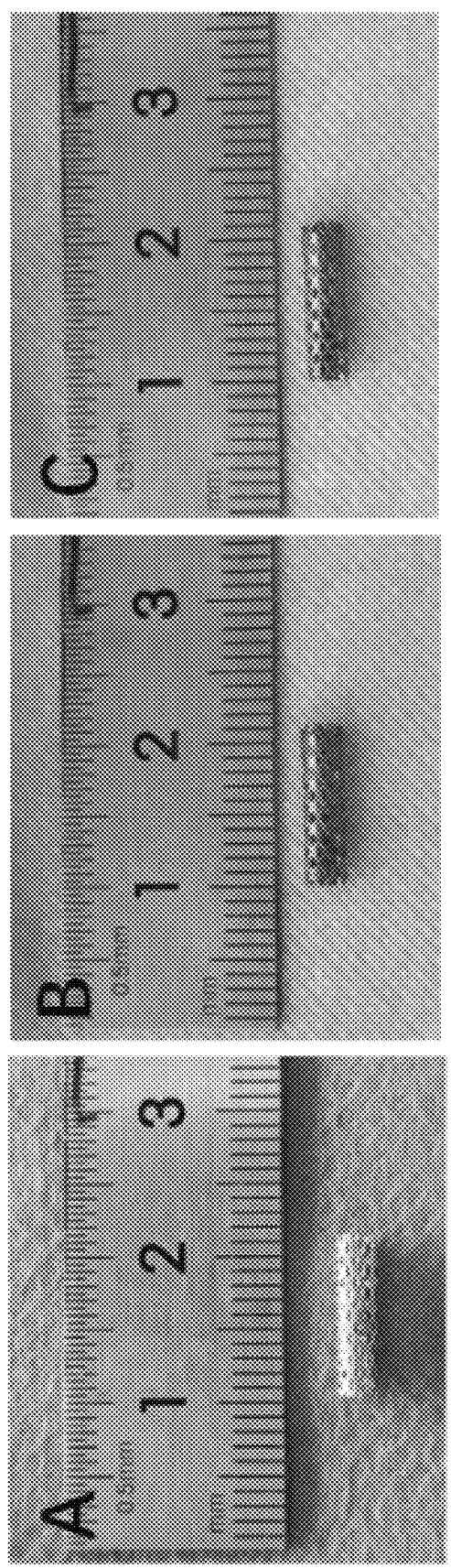
FIG. 11 shows a general view of a porous titanium mesh stent: A) a bare stent, B) a Ti+PEM+BMP-2 stent, C) a Ti+PEM+BMP-2 stent sterilized by γ-ray irradiation.

Refer to FIG. 11, the coating of the multilayer film slow-release system had little influence on the large appearance of the porous titanium bracket, and only changed a light reflection condition of the titanium bracket. There was no change in appearance of the bracket sterilized by gamma-ray irradiation sterilization.

Figure 12:
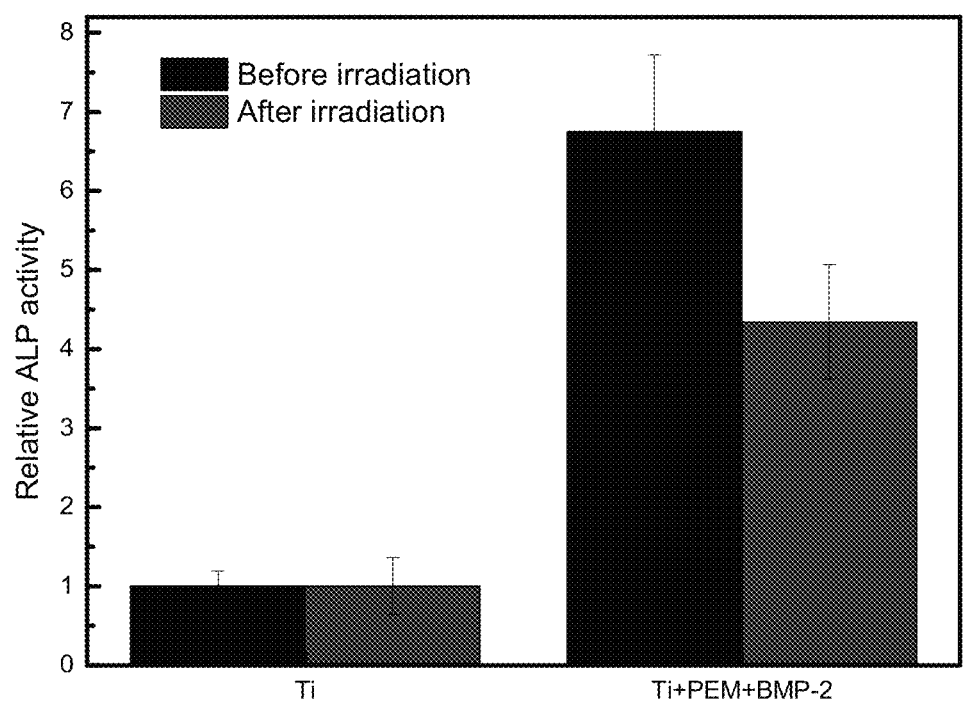
FIG. 12 shows ALP expression of bone marrow mesenchymal stem cells around the titanium stent before and after γ-irradiation sterilization (after 7 days of culture).

The bracket was put into a 24-pore plate to carry out osteogenic differentiation culture on the mesenchymal stem cells; and ALP was quantified through an ELISA kit 7 days after the culture, with the results listed in FIG. 12. Visibly, the sterilized Ti+PEM-BMP-2 bracket still had higher osteogenic induction activity which was consistent with the results of the previous planar titanium material.

Figure 13:
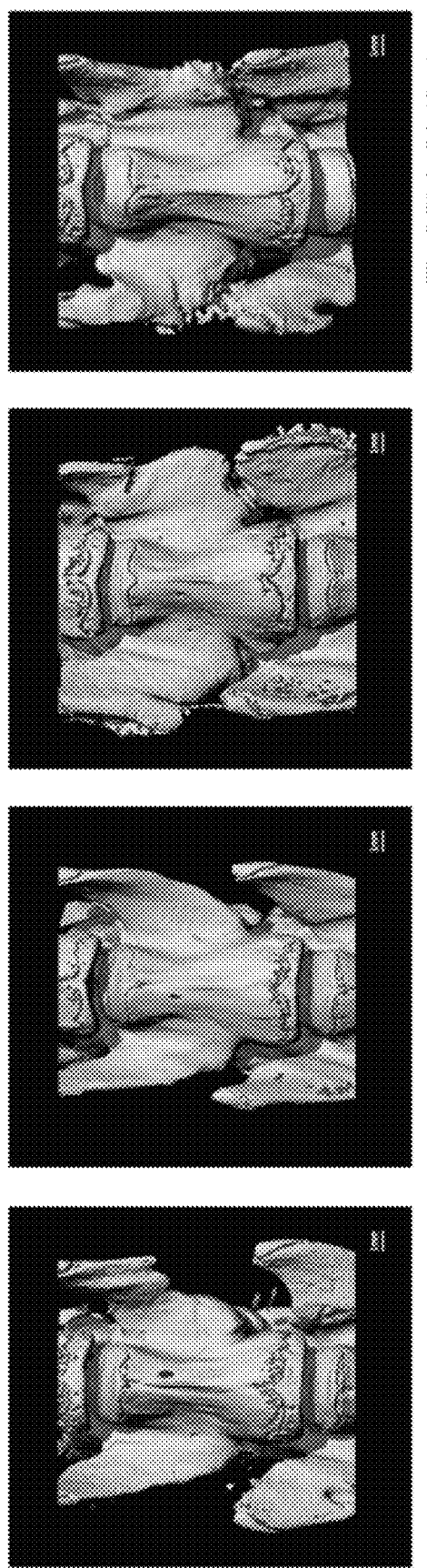
FIG. 13 shows Micro-CT reconstruction of a fusion condition between two transverse processes of rat caudal vertebra induced by the Ti+PEM+BMP-2 stent: γ-Ti+PEM+BMP-2 refers to Ti+PEM+BMP-2 sterilized by γ-ray irradiation.

The cylindrical porous titanium bracket was put between two transverse processes of a rat caudal vertebra to induce fusion of the two transverse processes. A vertebral tissue was taken four weeks later, and a bone tissue structure was reconstructed through Micro-CT; and as shown in FIG. 13, the Ti bracket was limited in fusion of intervertebral fusion, so that the two transverse processes were not fused; the titanium bracket coated with the multilayer film had certain induction effect on intervertebral fusion which was slightly increased. The osteogenic induction effect of the BMP-2 slow-release system was very obvious, so that the two transverse processes were completely fused before; and interestingly, the fusion condition between the two transverse processes sterilized through gamma-ray irradiation was similar to the unsterilized bracket. Visibly, the BMP-2 in the slow-release system lost part of activity in in-vitro detection through irradiation sterilization, but the kept activity still could achieve the effect of effectively inducing osteanagenesis in vivo.

In addition to the preferred embodiment, the present invention further has other embodiments. Various changes and modifications made by those skilled in the art shall fall within the scope as defined in the appended claims without departing from the spirit of the invention.

What is claimed is:

1. A method for constructing a bone morphogenetic protein slow-release system, comprising the following steps:
   I: activating a titanium material: washing and drying the titanium material, soaking the dried titanium material into a buffer solution containing dopamine, and reacting for 12-72 hours to obtain a polydopamine (PDA)-modified Ti base material;
   II: activating ceramic powder: dissolving the ceramic powder and the dopamine into the buffer solution, vibrating and dispersing, reacting for 12-72 hours under stirring, and centrifuging to remove large particles, thereby obtaining a polydopamine-modified ceramic particles (PDA@HA) solution;
   III: constructing a multilayer film: sequentially soaking the PDA-modified Ti base material in a positively-charged polyelectrolyte solution, a negatively-charged polyelectrolyte solution, a positively-charged polyelectrolyte solution and the polydopamine-modified ceramic particles solution for 8-15 min, and washing with water after soaking; and
   IV: soaking in a circulating mode: soaking and cleaning in step III by circulating operation with circulating times of n times, thereby obtaining a positively-charged polyelectrolyte, negatively-charged polyelectrolyte and PDA-modified ceramic particles multilayer film.

2. The method for constructing the bone morphogenetic protein slow-release system according to claim 1, wherein the positively-charged polyelectrolyte, negatively-charged polyelectrolyte and PDA-modified ceramic particles multilayer film is soaked in a cross-linking solution for 6-24 hours, then washed with water and dried to obtain a cross-linked multilayer film.

3. The method for constructing the bone morphogenetic protein slow-release system according to claim 1, wherein the buffer solution containing dopamine in step I is a Tris-HCl buffer solution with a dopamine concentration of 0.3-5.0 mg/mL, and a pH value of 8-9.

4. The method for constructing the bone morphogenetic protein slow-release system according to claim 1, wherein the ceramic powder in step II is any one of hydroxyapatite, bioactive glass, calcium phosphate, aluminum oxide or zirconium oxide, and a weight ratio of the ceramic powder to the dopamine is (8-15) to 1.

5. The method for constructing the bone morphogenetic protein slow-release system according to claim 1, wherein the positively-charged polyelectrolyte solution in step III is any one of a chitosan solution or a polylysine solution, with a concentration of 0.3-5.0 mg/mL; and/or, the negatively-charged polyelectrolyte solution is any one of a glucan solution, a heparin solution, a heparan sulfate solution, an alginic acid solution, a hyaluronic acid solution, a collagen solution, a gelatin solution, a carrageenan solution or a cellulose acetate solution, with a concentration of 0.3-5.0 mg/mL; and/or, the PDA@HA polydopamine-modified ceramic particles solution is a solution with a polydopamine-modified ceramic particle concentration of 0.3-5.0 mg/mL.

6. The method for constructing the bone morphogenetic protein slow-release system according to claim 1, wherein the circulating times n are greater than 3.

7. The method for constructing the bone morphogenetic protein slow-release system according to claim 2, wherein the cross-linking solution is at least one of a carbodiimide solution with a concentration of 25-70 mg/mL, a thiosuccimide solution with a concentration of 5-25 mg/mL, a glutaraldehyde solution with a mass concentration of 2.5% or a genipin solution with a mass concentration of 1-4%.

* * * * *